US012697085B2

(12) United States Patent
Masahashi et al.

(10) Patent No.: US 12,697,085 B2
(45) Date of Patent: Aug. 4, 2026

(54) X-RAY DIAGNOSIS APPARATUS

(71) Applicant: Canon Kabushiki Kaisha, Tokyo (JP)

(72) Inventors: Junji Masahashi, Otawara (JP);
Hiroaki Sato, Nasushiobara (JP);
Yasushi Sakai, Kawasakishi (JP);
Yasuhiro Sugawara, Nasushiobara
(JP); Makoto Ishii, Nasushiobara (JP);
Atsushi Kotani, Nasushiobara (JP);
Norio Soutsuka, Nasushiobara (JP);
Shoji Yashiro, Nasushiobara (JP);
Tatsuaki Kodaka, Nasushiobara (JP)

(73) Assignee: Canon Kabushiki Kaisha, Tokyo (JP)

( * ) Notice: Subject to any disclaimer, the term of this
patent is extended or adjusted under 35
U.S.C. 154(b) by 194 days.

(21) Appl. No.: 18/504,521

(22) Filed: Nov. 8, 2023

(65) Prior Publication Data

US 2024/0156428 A1 May 16, 2024

(30) Foreign Application Priority Data

Nov. 10, 2022 (JP) ................................. 2022-180492

(51) Int. Cl.
*A61B 6/00* (2006.01)
*A61B 6/46* (2024.01)
(52) U.S. Cl.
CPC .............. *A61B 6/545* (2013.01); *A61B 6/463*
(2013.01); *A61B 6/469* (2013.01); *A61B 6/488*
(2013.01)
(58) Field of Classification Search
CPC ......... A61B 6/545; A61B 6/463; A61B 6/469;
A61B 6/488
See application file for complete search history.

(56) References Cited

U.S. PATENT DOCUMENTS

| | | | |
|---|---|---|---|
| 11,278,253 B2 | 3/2022 | Sato et al. | |
| 2010/0290592 A1* | 11/2010 | Yamada | A61B 6/542 |
| | | | 378/114 |
| 2015/0250441 A1* | 9/2015 | Okuno | A61B 6/547 |
| | | | 378/62 |
| 2019/0343479 A1 | 11/2019 | Sato et al. | |
| 2021/0353242 A1* | 11/2021 | Park | A61B 6/467 |
| 2022/0015734 A1* | 1/2022 | Maack | A61B 6/466 |

(Continued)

FOREIGN PATENT DOCUMENTS

| | | | | |
|---|---|---|---|---|
| EP | 2497424 A1 * | 9/2012 | ............... | A61B 6/06 |
| EP | 3254626 A1 * | 12/2017 | ............... | A61B 6/04 |

(Continued)

*Primary Examiner* — Drew A Dunn
(74) *Attorney, Agent, or Firm* — Oblon, McClelland,
Maier & Neustadt, L.L.P.

(57) ABSTRACT

An X-ray diagnosis apparatus according to an embodiment
includes: an X-ray generator configured to emit X-rays; an
X-ray detector having a detection surface parallel to a first
direction and being movable in the first direction and in a
second direction orthogonal to the first direction and parallel
to the detection surface; and processing circuitry configured
to set a plurality of imaging ranges touching each other on
the basis of reference information, to cause the X-rays to be
emitted from the X-ray generator to each of the plurality of
imaging ranges while sequentially moving the X-ray detec-
tor, and to generate X-ray images respectively correspond-
ing to the plurality of imaging ranges, on the basis of a
detection signal resulting from the X-ray detector detecting
the X-rays.

8 Claims, 16 Drawing Sheets

(56)     References Cited

U.S. PATENT DOCUMENTS

| | | | | |
|---|---|---|---|---|
| 2022/0280129 A1* | 9/2022 | Sun | ...................... | A61B 6/4452 |
| 2023/0000456 A1* | 1/2023 | Nakanishi | .............. | A61B 6/545 |
| 2023/0169666 A1* | 6/2023 | Pati | ..................... | A61B 6/5241 |
| | | | | 382/132 |
| 2023/0320590 A1* | 10/2023 | Shi | ...................... | A61B 6/0492 |
| | | | | 600/300 |
| 2024/0081765 A1* | 3/2024 | Kitano | ................... | A61B 6/544 |
| 2024/0156428 A1* | 5/2024 | Masahashi | ............. | A61B 6/545 |
| 2024/0341713 A1* | 10/2024 | Zhang | ................... | A61B 6/488 |

FOREIGN PATENT DOCUMENTS

| | | | |
|---|---|---|---|
| JP | 7-136148 A | 5/1995 |
| JP | 2015-47194 A | 3/2015 |
| JP | 2019-198375 A | 11/2019 |

* cited by examiner

D1

R51

R52

Z
X ← ⊙ Y

X-RAY DIAGNOSIS APPARATUS

CROSS-REFERENCE TO RELATED APPLICATIONS

This application is based upon and claims the benefit of priority from Japanese Patent Application No. 2022-180492, filed on Nov. 10, 2022; the entire contents of which are incorporated herein by reference.

FIELD

Embodiments described herein relate generally to an X-ray diagnosis apparatus.

BACKGROUND

The size of X-ray detectors included in X-ray diagnosis apparatuses is finite. The size of an imaging range that can be imaged with an X-ray emission at a time is also finite. For this reason, depending on the site to be examined (hereinafter, "examined site"), it may not be possible in some situations to image the entire site with an X-ray emission at one time. For example, when the spine or a leg is an examined site, the size of the examined site may exceed the size of the imaging range.

Known as a technique that makes it possible to observe the entire examined site even when the site is large is long image stitching. The long image stitching technique makes it possible to provide an X-ray image exhibiting the entire examined site even when the site is large, by setting a plurality of imaging ranges touching each other so as to take a plurality of X-ray images and combining the X-ray images together.

A problem to be solved by the present disclosure is to provide an X-ray diagnosis apparatus capable of setting a plurality of imaging ranges for long image stitching, easily and appropriately.

An X-ray diagnosis apparatus according to an embodiment includes: an X-ray generator configured to emit X-rays; an X-ray detector having a detection surface parallel to a first direction and being movable in the first direction and in a second direction orthogonal to the first direction and parallel to the detection surface; an imaging condition setting unit configured to set a plurality of imaging ranges touching each other on the basis of reference information; an imaging controlling unit configured to cause the X-rays to be emitted from the X-ray generator to each of the plurality of imaging ranges while sequentially moving the X-ray detector; and an image generating unit configured to generate X-ray images respectively corresponding to the plurality of imaging ranges, on the basis of a detection signal resulting from the X-ray detector detecting the X-rays.

DETAILED DESCRIPTION

An X-ray diagnosis apparatus according to an embodiment comprises: an X-ray generator configured to emit X-rays; an X-ray detector having a detection surface parallel to a first direction and being movable in the first direction and in a second direction orthogonal to the first direction and parallel to the detection surface; and processing circuitry configured to set a plurality of imaging ranges touching each other on the basis of reference information, to cause the X-rays to be emitted from the X-ray generator to each of the plurality of imaging ranges while sequentially moving the X-ray detector, and to generate X-ray images respectively corresponding to the plurality of imaging ranges, on the basis of a detection signal resulting from the X-ray detector detecting the X-rays.

Exemplary embodiments of the X-ray diagnosis apparatus will be explained in detail below, with reference to the accompanying drawings.

Figure 1:
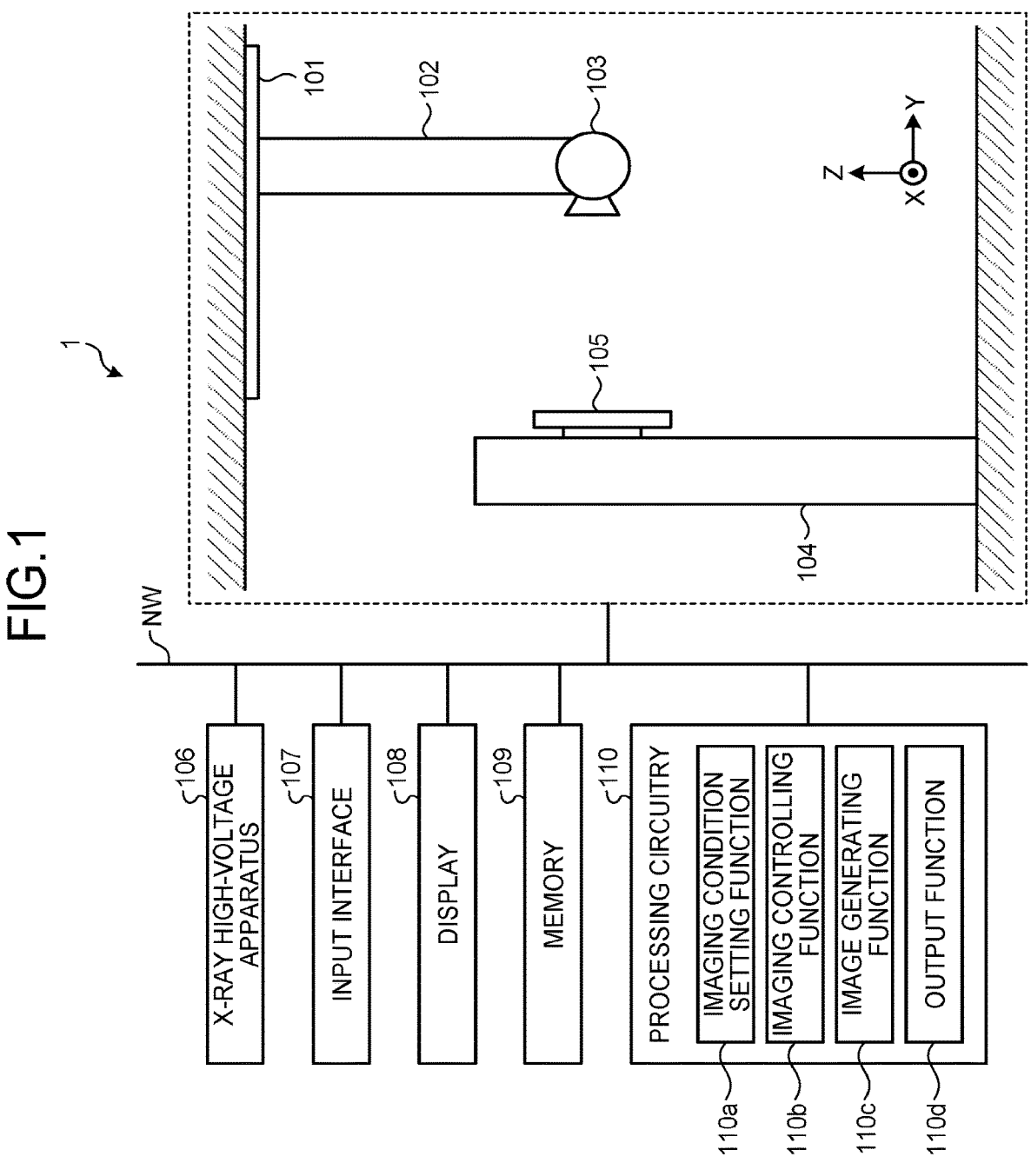
FIG. 1 is a block diagram illustrating an exemplary configuration of an X-ray diagnosis apparatus according to a first embodiment.

In an embodiment of the present disclosure, an X-ray diagnosis apparatus 1 in FIG. 1 will be explained as an example. FIG. 1 is a block diagram illustrating an exemplary configuration of the X-ray diagnosis apparatus 1 according to a first embodiment. The X-ray diagnosis apparatus 1 includes a rail 101, a holding apparatus 102, an X-ray generator 103, a holding apparatus 104, an X-ray detector 105, an X-ray high-voltage apparatus 106, an input interface 107, a display 108, a memory 109, and processing circuitry 110. the display 108 is an example of the display unit.

In FIG. 1, while a floor surface or the like is used as a reference, a vertical direction will be referred to as a Z direction. The vertical direction and the Z direction are each an example of the first direction. As illustrated in FIG. 1, the X-ray detector 105 is arranged so that a detection surface thereof extends parallel to the Z direction. Further, an X direction is the direction orthogonal to the Z direction and parallel to the detection surface of the X-ray detector 105. The X direction may be referred to as a left-and-right direction. The left-and-right direction and the X direction are each an example of the second direction. A Y direction is the direction orthogonal to the X direction and the Z direction. An X-ray emission from the X-ray generator 103 to the X-ray detector 105 is performed along a direction substantially parallel to the Y direction.

The rail 101 is provided on the ceiling of an examination room so as to extend along the Y direction. The holding apparatus 102 is movable in the Y direction along the rail 101. The holding apparatus 102 is configured to hold the X-ray generator 103 so as to be movable in the X direction and the Z direction.

The X-ray generator 103 is an apparatus configured to generate X-rays. For example, the X-ray generator 103 includes an X-ray tube and an X-ray limiter. The X-ray tube is a vacuum tube having a negative pole (a filament) that generates thermo electrons and a positive pole (a target) that generates the X-rays upon collision of the thermo electrons therewith. More specifically, by using high voltage supplied from the X-ray high-voltage apparatus 106, the X-ray tube is configured to generate the X-rays by causing the thermo electrons released from the negative pole to accelerate toward the positive pole and to collide therewith. Further, the X-ray limiter is configured, for example, to form an emission opening by using four slidable limiting blades. In this situation, the limiting blades are plate-like members configured by using lead or the like. The X-ray limiter is configured to control the shape and the size of the emission opening by sliding the limiting blades so as to narrow down an emission range of the X-rays generated by the X-ray tube.

The holding apparatus 104 is configured to hold the X-ray detector 105 so as to be movable in the X direction and the Z direction. Alternatively, the holding apparatus 104 may be configured so as to be movable in the X direction, while holding the X-ray detector 105 so as to be movable in the Z direction. For example, the X-ray detector 105 may be an X-ray Flat Panel Detector (FPD) including detecting elements arranged in a matrix formation. The X-ray detector 105 is configured to detect X-rays that were emitted from the X-ray generator 103 and have passed through an examined subject (hereinafter, "patient") and to output a detection signal corresponding to a detected X-ray amount to the processing circuitry 110. The X-ray detector 105 may be a detector of an indirect conversion type including a grid, a scintillator array, and an optical sensor array or may be a detector of a direct conversion type including a semiconductor element configured to convert X-rays that have become incident thereto into an electrical signal.

Figure 2:
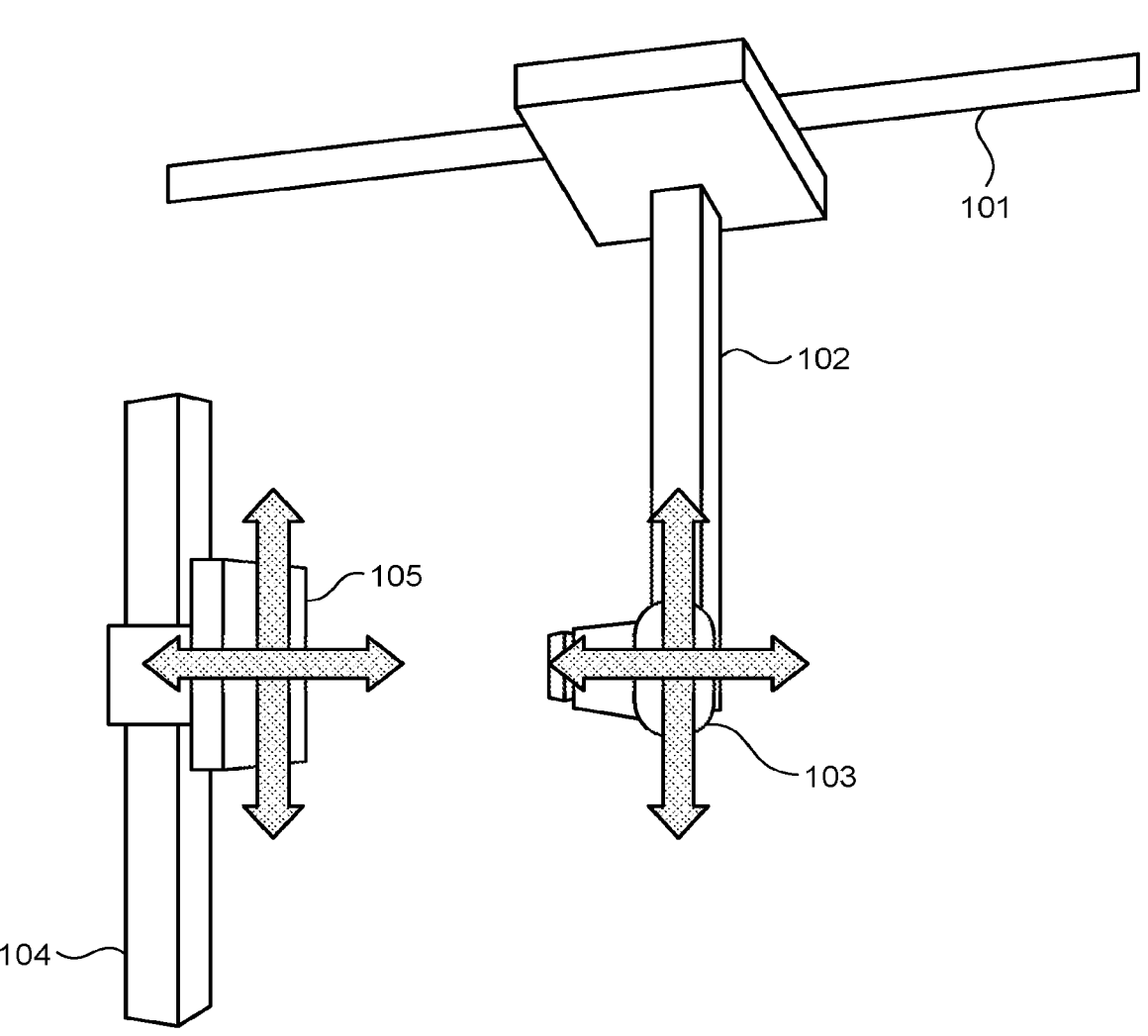
FIG. 2 is a drawing illustrating movable directions of an X-ray generator and an X-ray detector according to the first embodiment.

In other words, the X-ray generator 103 and the X-ray detector 105 are configured so as to be movable in at least the Z direction and the X direction, as indicated with the arrows in FIG. 2. As mechanisms for moving the X-ray generator 103 and the X-ray detector 105, FIGS. 1 and 2 illustrate the rail 101, the holding apparatus 102, and the holding apparatus 104. However, specific moving mechanisms are not particularly limited and may arbitrarily be modified, as long as it is possible to move the X-ray generator 103 and the X-ray detector 105 in the Z direction and the X direction.

Under control of the processing circuitry 110, the X-ray high-voltage apparatus 106 is configured to supply the high voltage to the X-ray generator 103. For example, the X-ray high-voltage apparatus 106 includes: a high-voltage generating apparatus having electric circuitry such as a transformer and a rectifier or the like and configured to generate the high voltage; and an X-ray controlling apparatus configured to control X-ray tube voltage, X-ray tube current, and an emission time period. Further, the high-voltage generating apparatus may be of a transformer type or may be of an inverter type.

The input interface 107 is configured to receive various types of input operations from a user, to convert the received input operations into electrical signals, and to output the electrical signals to the processing circuitry 110. For example, the input interface 107 is realized by using a mouse, a keyboard, a trackball, a switch, a button, a joystick, a touchpad on which input operations can be performed by touching an operation surface thereof, a touch screen in which a display screen and a touchpad are integrally formed, contactless input circuitry using an optical sensor, audio input circuitry, and/or the like. Further, the input interface 107 may be configured by using a tablet terminal or the like capable of wirelessly communicating with the processing circuitry 110. Furthermore, the input interface 107 may be circuitry configured to receive the input operations from the user through motion capture. In an example, as an input operation, the input interface 107 may be capable of receiving a body movement, a line of sight, or the like of the user, by processing a signal obtained via a tracker or an image acquired of the user. Further, the input interface 107 does not necessarily have to include physical component parts such as a mouse, a keyboard, and/or the like. For instance, possible examples of the input interface 107 include electrical signal processing circuitry configured to receive an electrical signal corresponding to an input operation from an external input mechanism provided separately from the X-ray diagnosis apparatus 1 and to output the electrical signal to the processing circuitry 110.

The display 108 is configured to display various types of information. For example, the display 108 is configured to display a Graphical User Interface (GUI) for receiving various types of instructions, settings, and the like from the user via the input interface 107. Further, the display 108 is configured to display X-ray images having been taken. For example, the display 108 may be a liquid crystal display or a Cathode Ray Tube (CRT) display. The display 108 may be of a desktop type or may be configured by using a tablet terminal or the like capable of wirelessly communicating with the processing circuitry 110.

For example, the memory 109 is realized by using a semiconductor memory element such as a Random Access Memory (RAM) or a flash memory, or a hard disk, an optical disc, or the like. For example, the memory 109 is configured to store therein data of the taken X-ray images. Further, the memory 109 is configured to store therein a program used by the circuitry included in the X-ray diagnosis apparatus 1 for realizing the functions thereof. The memory 109 may be realized by using a server group (a cloud) connected to the X-ray diagnosis apparatus 1 via a network NW.

The processing circuitry 110 is configured to control operations of the entirety of the X-ray diagnosis apparatus 1, by functioning as an imaging condition setting function 110a, an imaging controlling function 110b, an image generating function 110c, and an output function 110d. The imaging condition setting function 110a is an example of the imaging condition setting unit. The imaging controlling function 110b is an example of the imaging controlling unit. The image generating function 110c is an example of the image generating unit. The output function 110d is an example of the output unit. For example, by reading and executing a program corresponding to the imaging condition setting function 110a from the memory 109, the processing circuitry 110 is configured to function as the imaging condition setting function 110a. Similarly, the processing circuitry 110 is configured to function as the imaging controlling function 110b, the image generating function 110c, and the output function 110d.

For example, the imaging condition setting function 110a is configured to set a plurality of imaging ranges for long image stitching. Further, the imaging controlling function 110b is configured to acquire the detection signal by causing the X-rays to be emitted from the X-ray generator 103 to each of the plurality of imaging ranges that were set, while sequentially moving the X-ray detector 105. Further, the image generating function 110c is configured to generate X-ray images respectively corresponding to the plurality of imaging ranges, on the basis of the acquired detection signal and to further store the generated X-ray images into the memory 109. Further, the output function 110d is configured to control outputs of various types of information. For example, the output function 110d is configured to control what is displayed on the display 108. Further, the output function 110d may transmit the X-ray images to an external apparatus via the network NW so as to have the X-ray images saved. Examples of the external apparatus include a server of a Picture Archiving and Communication System (PACS).

In the X-ray diagnosis apparatus 1 illustrated in FIG. 1, the processing functions are stored in the memory 109 in the form of computer-executable programs. The processing circuitry 110 is a processor configured to realize the functions corresponding to the programs, by reading and executing the programs from the memory 109. In other words, the processing circuitry 110 that has read the programs has the functions corresponding to the read programs.

Although the example was explained with reference to FIG. 1 in which the single piece of processing circuitry (i.e., the processing circuitry 110) realizes the imaging condition setting function 110a, the imaging controlling function 110b, the image generating function 110c, and the output function 110d, it is also acceptable to structure the processing circuitry 110 by combining together a plurality of independent processors, so that the functions are realized as a result of the processors executing the programs. Further, the processing functions of the processing circuitry 110 may be realized as being distributed among or integrated into one or more pieces of processing circuitry, as appropriate.

Furthermore, the processing circuitry 110 may be configured to realize the functions, by using a processor of an external apparatus connected via the network NW. For example, the processing circuitry 110 may be configured to realize the functions illustrated in FIG. 1, by reading and executing the programs corresponding to the functions from the memory 109 and also using a server group (a cloud) connected to the X-ray diagnosis apparatus 1 via the network NW as computation resources.

An overall configuration of the X-ray diagnosis apparatus 1 has thus been explained. The X-ray diagnosis apparatus 1 structured as described above is configured to execute the long image stitching. In the following sections, as an example, a situation where the spine is an examined site will be explained.

Figure 3A:
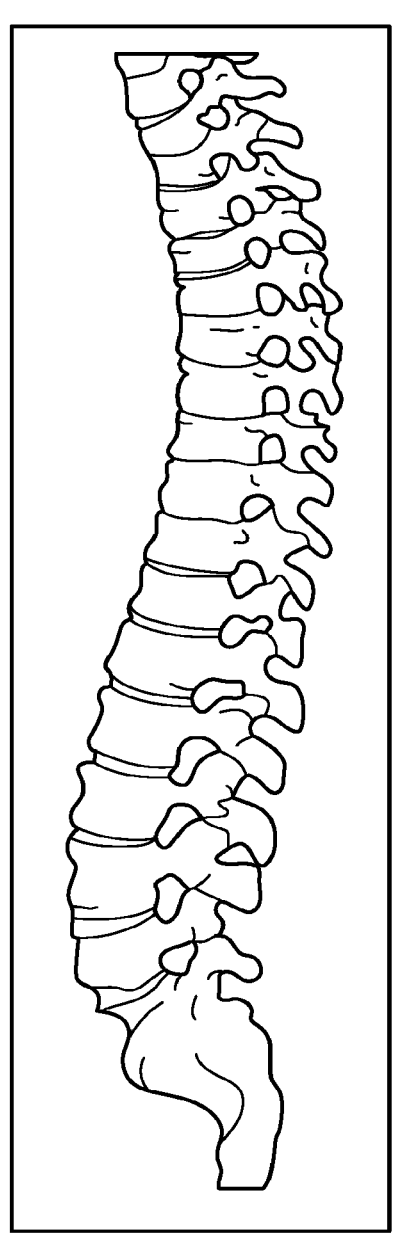
FIG. 3A is a drawing illustrating an example of the spine in the first embodiment.
Figure 3A:
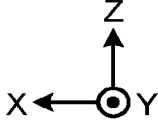

FIG. 3A is a drawing illustrating the spine of a patient from a side. More specifically, the drawing illustrates the spine taken on a sagittal plane. As illustrated in FIG. 3A, the spine is formed to have a gentle S-shaped curve in many situations. When an image on a sagittal plane is to be taken, the patient is positioned between the X-ray generator 103 and the X-ray detector 105, so that the patient faces to the right or the left as viewed from the X-ray generator 103. FIG. 3A illustrates an example in which the patient is imaged while facing to the left (i.e., a +X direction) as viewed from the X-ray generator 103.

Figure 3B:
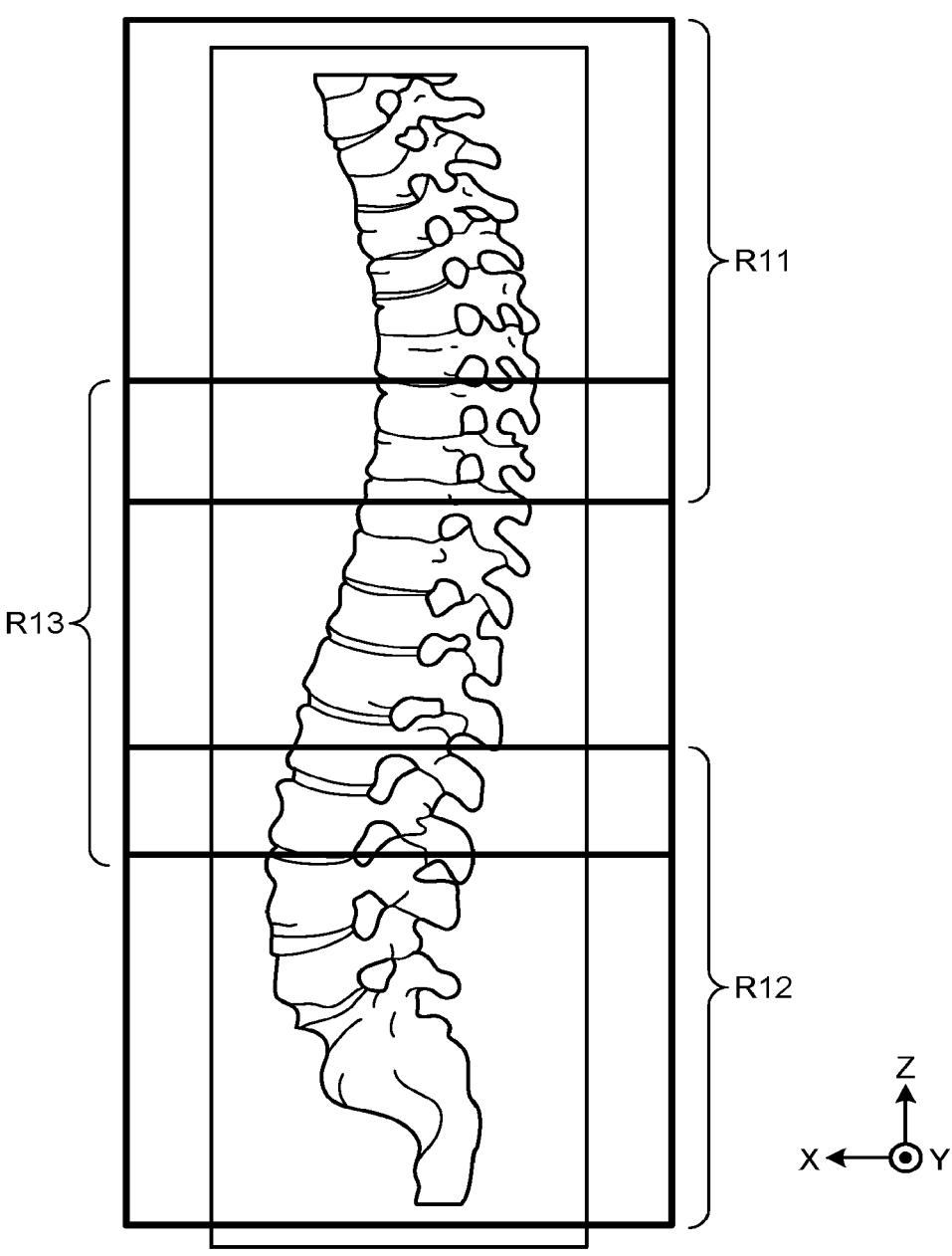
FIG. 3B is a drawing illustrating a plurality of imaging ranges according to the first embodiment.

When the long image stitching is to be performed on the spine in FIG. 3A, three imaging ranges (an imaging range R11, an imaging range R12, and an imaging range R13) are set, as illustrated in FIG. 3B, for example. Although FIG. 3B illustrates the imaging ranges superimposed on the spine for the sake of convenience in the explanations, the X-ray image of the spine has not yet been acquired at the stage of setting the imaging ranges. For example, the X-ray diagnosis apparatus 1 is capable of presenting the user (e.g., a medical doctor) with the set imaging ranges, through a laser emission of visible light indicating the imaging ranges, onto the body surface or clothing of the patient.

Figure 3C:
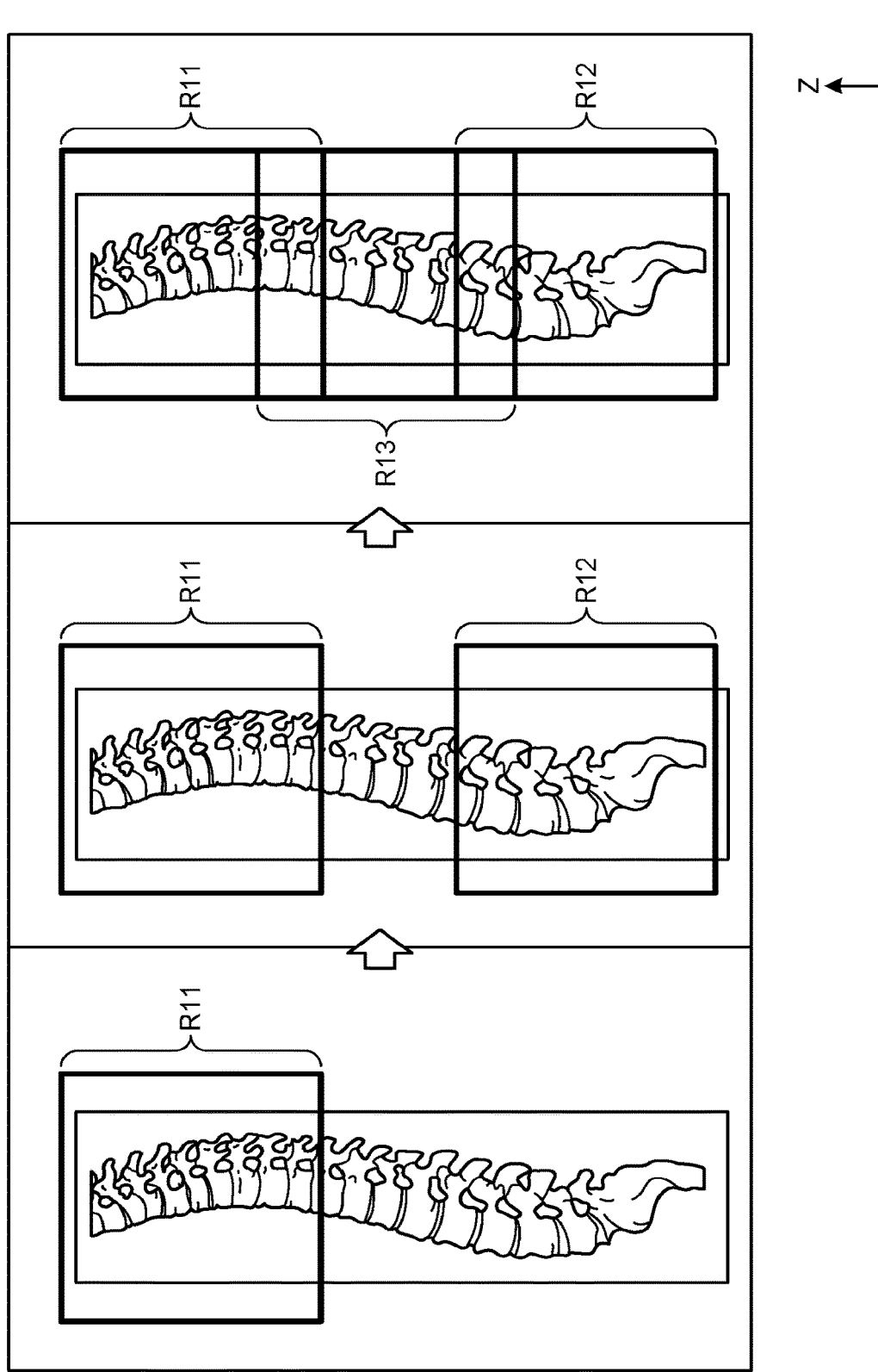
FIG. 3C is a drawing for explaining a method for setting the plurality of imaging ranges according to the first embodiment.

More specifically, to begin with, as illustrated in the left section of FIG. 3C, the imaging range R11 is set so as to contain the upper end of the spine in terms of the Z direction. For example, the X-ray diagnosis apparatus 1 is configured to carry out a laser emission of visible light indicating the imaging range, onto the patient. For example, the X-ray generator 103 is provided with a light source, so that the laser emission of the visible light indicating the imaging range is started from the light source. In that situation, by moving the position of the X-ray generator 103, it is possible to adjust the position of the imaging range. For example, the user (e.g., the medical doctor) determines the position of the imaging range R11 so as to contain the upper end of the spine, by moving the position of the X-ray generator 103 via the input interface 107, while looking at the patient and estimating the position of the spine.

Similarly, the user (e.g., the medical doctor) sets the imaging range R12 so as to contain the lower end of the spine in terms of the Z direction. After that, the imaging range R13 is set so as to connect the imaging range R11 and the imaging range R12 together. The imaging range R13 may be set by the user (i.e., the medical doctor) or may be automatically set by the apparatus. As illustrated in FIGS. 3B and 3C, the imaging range R11, the imaging range R12, and the imaging range R13 are a plurality of imaging ranges touching each other.

Figure 3D:
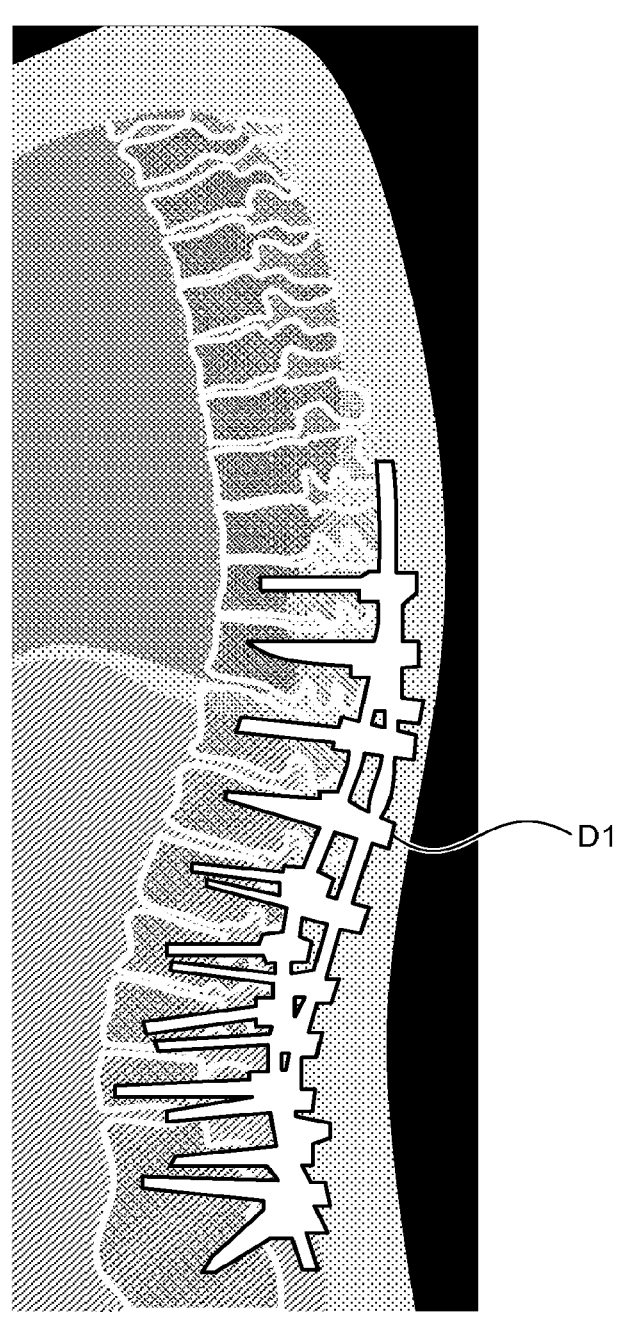
FIG. 3D is a drawing illustrating an example of a long stitched image according to the first embodiment.
Figure 3D:
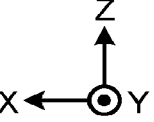

After the imaging ranges are set, the X-ray diagnosis apparatus 1 is configured to generate X-ray images respectively corresponding to the imaging ranges, by causing X-rays to be emitted from the X-ray generator 103 to each of the imaging ranges R11, R12, and R13, while sequentially moving the X-ray detector 105. The generated plurality of X-ray images are combined together so as to generate a long stitched image as illustrated in FIG. 3D. In the long stitched image, the entire spine is exhibited so that the user (e.g., the medical doctor) is able to evaluate the state of the spine and/or to make a treatment plan. In FIG. 3D, the spine is treated by using a fixture D1.

In this situation, as illustrated in FIG. 3A also, even when the patient does not have a particular disease, the spine is curved. To have the entire spine contained in a long stitched image, the user (e.g., a medical doctor) would need to set the imaging ranges while paying attention to the extent and the directions of the curve. More specifically, starting with the stage of setting the imaging range R11, the user would need to determine the position of the imaging range R11 in terms of the X direction, while being careful so that the spine would not stick out of the imaging range R12 or the imaging range R13 to be set subsequently.

Figure 4A:
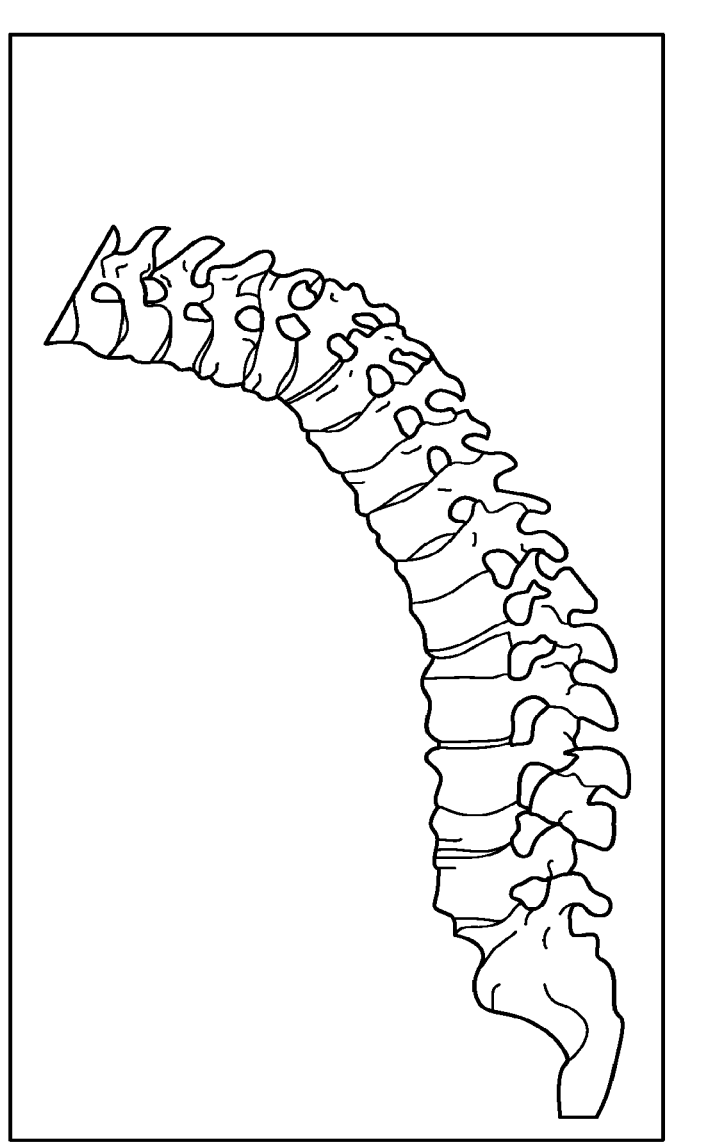
FIG. 4A is a drawing illustrating another example of the spine in the first embodiment.
Figure 4A:
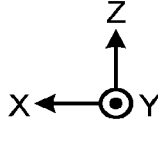

Further, in examples of patients having a disease, the spine may have a larger curve. In an example, FIG. 4A

Figure 4B:
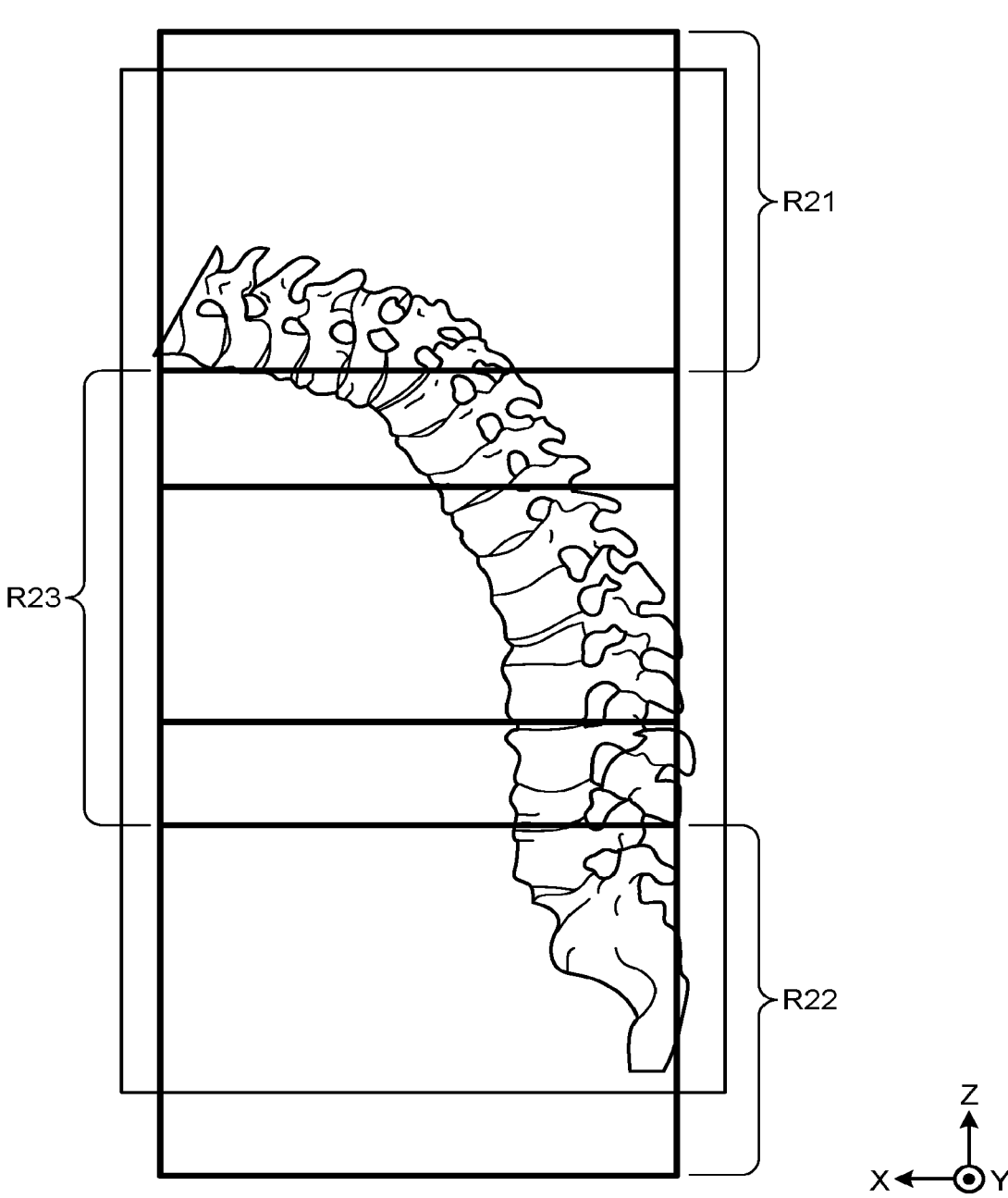
FIG. 4B is a drawing illustrating a plurality of imaging ranges according to the first embodiment.
Figure 4C:
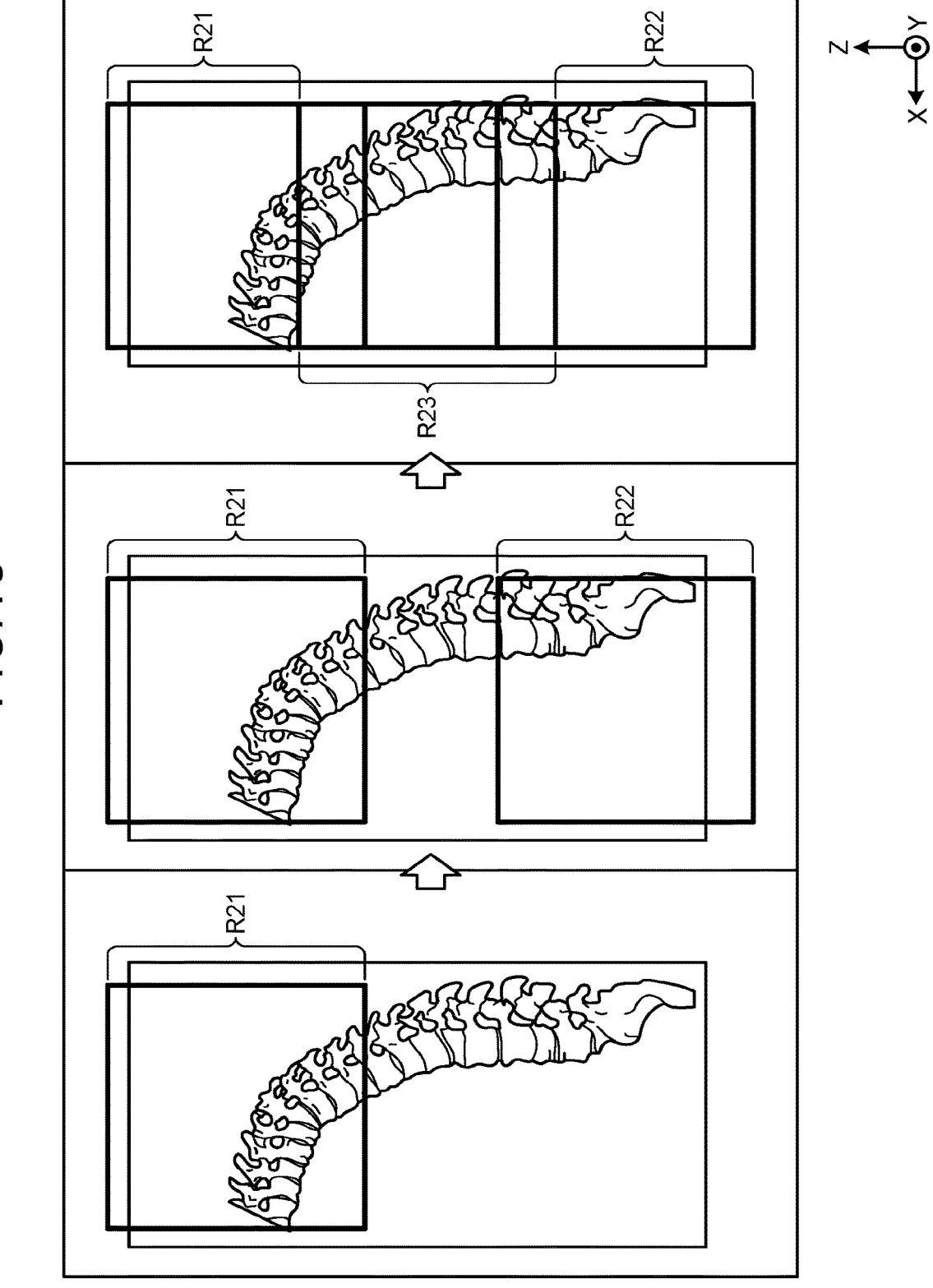
FIG. 4C is a drawing for explaining a method for setting the plurality of imaging ranges according to the first embodiment.
Figure 4D:
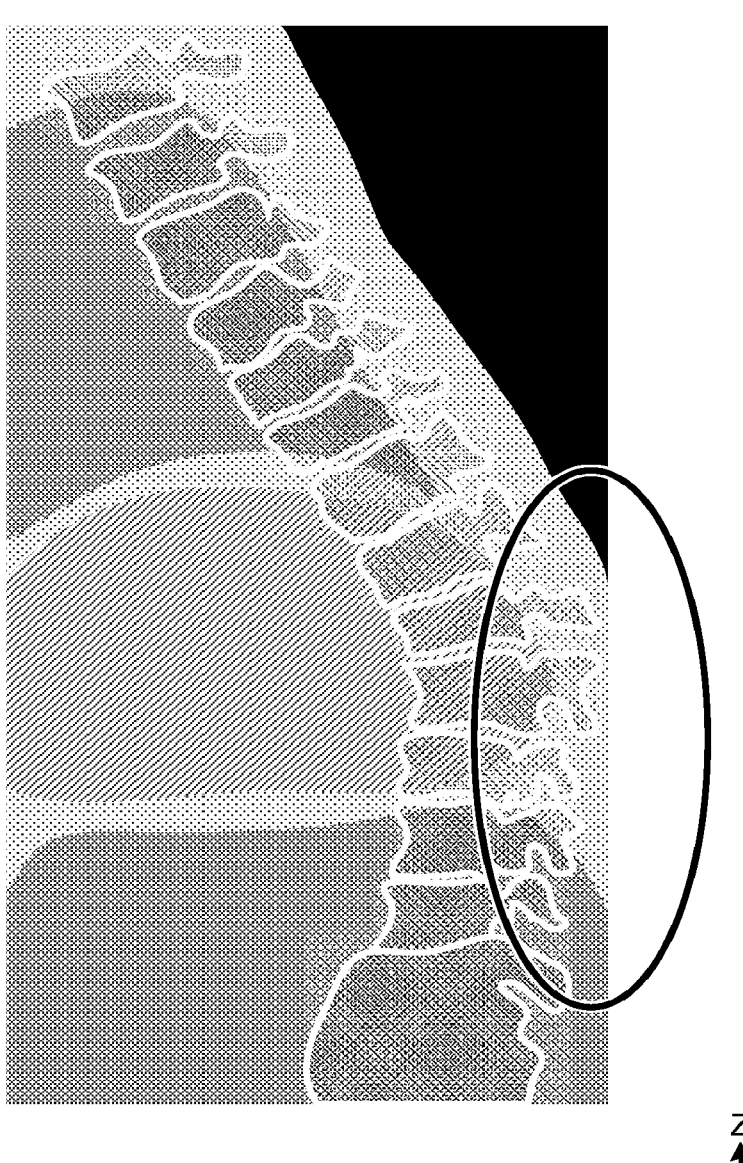
FIG. 4D is a drawing illustrating another example of a long stitched image according to the first embodiment.

7 illustrates the spine of a patient having kyphosis. Further, FIGS. 4B and 4C illustrate examples in which three imaging ranges (an imaging range R21, an imaging range R22, and an imaging range R23) are set, similarly to the examples in FIGS. 3B and 3C. With kyphosis, because the spine has a width in the X direction, even when the imaging ranges are carefully set, the spine might stick out of the long stitched image as indicated in the oval region in the long stitched image in FIG. 4D.

To cope with this situation, the imaging condition setting function 110a according to the embodiment is configured to set a first imaging range so that the upper end of the spine in terms of the Z direction is contained substantially at the center thereof in terms of the X direction; and a second imaging range so that the lower end of the spine in terms of the Z direction is contained substantially at the center thereof in terms of the X direction, and is configured to set at least one imaging range that connects these imaging ranges together. This configuration makes it possible to set the imaging range easily and appropriately even when the spine has a large curve.

Figure 5:
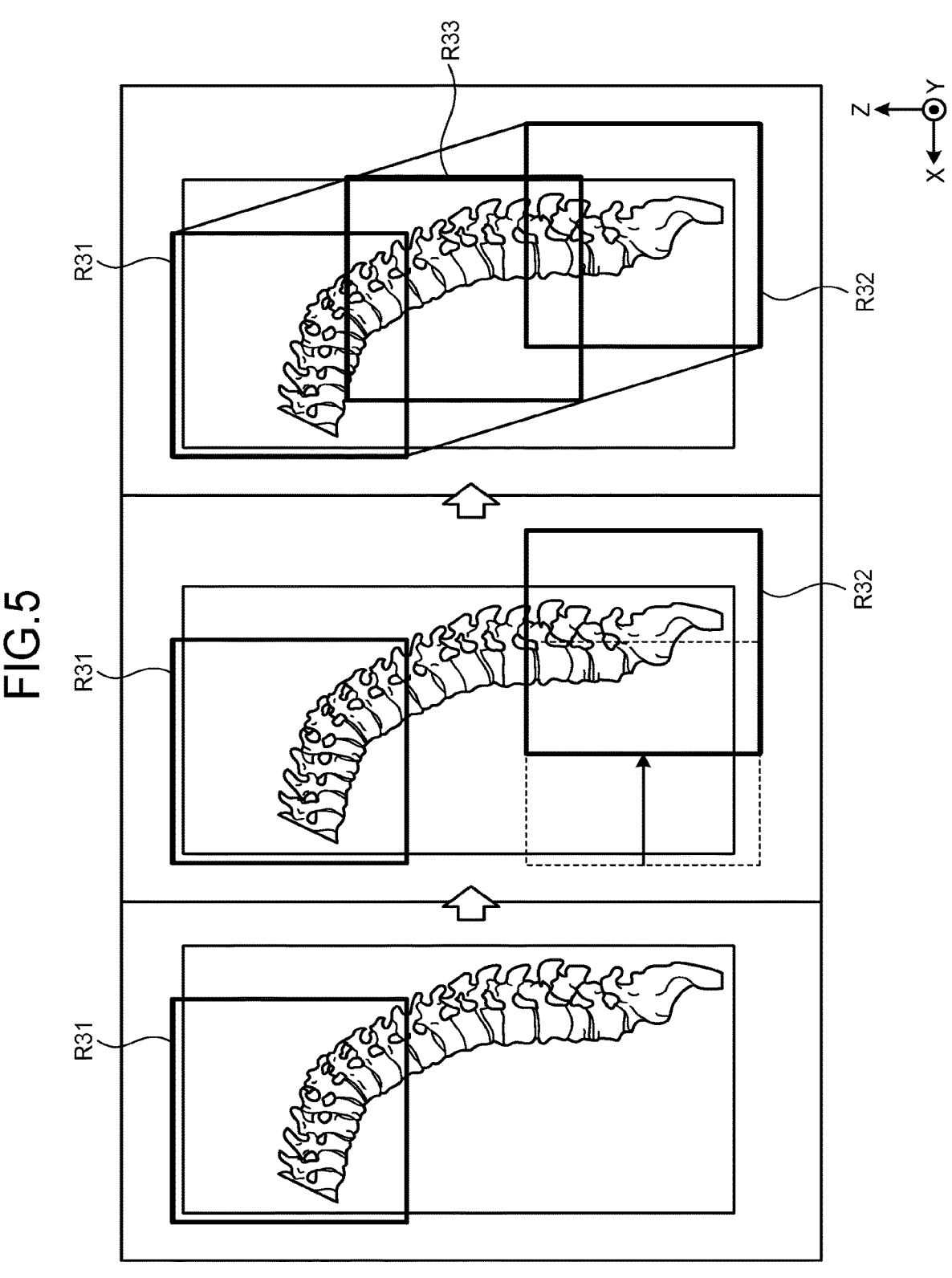
FIG. 5 is a drawing for explaining a method for setting a plurality of imaging ranges according to the first embodiment.

To begin with, the imaging condition setting function 110a is configured, as illustrated in the left section of FIG. 5, for example, to set an imaging range R31 so that the upper end of the spine of the patient in terms of the Z direction is contained substantially at the center thereof in terms of the X direction. For example, the user (e.g., a medical doctor) moves the position of the X-ray generator 103 via the input interface 107, while referring to the visible light indicating the imaging range and realized with the laser emission from the light source provided for the X-ray generator 103, and further performs an input operation to confirm a position determined to be appropriate. On the basis of the input operation of the user, the imaging condition setting function 110a is able to set the imaging range R31.

As for the phrase "substantially at the center thereof in terms of the X direction", the position does not necessarily need to be exactly at the center, as indicated in the left section of FIG. 5. For example, the imaging condition setting function 110a is configured to set the imaging range R31, so that the upper end of the spine in terms of the Z direction is positioned within the range other than the areas accounting for "5%" at the two ends of the imaging range R31 in terms of the X direction. Alternatively, for example, the imaging condition setting function 110a may be configured to set, as the imaging range R31, an imaging range determined by the user to contain the upper end of the spine in terms of the Z direction, substantially at the center thereof in terms of the X direction.

Although setting the imaging range R31 requires the user operation, the burden of the work is reduced. More specifically, at the time of setting the position of the imaging range R31, the user does not need to consider the overall shape of the spine, and needs to consider only the position of the upper end thereof. In other words, setting the imaging range R31 has fewer items to pay attention to and is easier than setting the imaging range R11 or the imaging range R21 described above.

Subsequently, as illustrated in the middle section of FIG. 5, the imaging condition setting function 110a is configured to set an imaging range R32 so that the lower end of the spine in terms of the Z direction is contained substantially at the center thereof in terms of the X direction. In this situation, the position of the imaging range R32 in the X direction may be out of alignment with the imaging range R31. In other words, because the X-ray diagnosis apparatus 1 is configured so that the X-ray detector is movable in the Z direction and the X direction, it is possible to set a plurality of imaging positions that are out of alignment with each other in the X direction. For example, the user (e.g., the medical doctor) moves the position of the X-ray generator 103 via the input interface 107, while referring to the visible light indicating the imaging range and realized with the laser emission from the light source provided for the X-ray generator 103, and further performs an input operation to confirm a position determined to be appropriate. On the basis of the input operation of the user, the imaging condition setting function 110a is able to set the imaging range R32. The imaging range R31 and the imaging range R32 are each an example of the reference information.

After that, as illustrated in the right section of FIG. 5, the imaging condition setting function 110a sets an imaging range R33 that connects together the imaging range R31 and the imaging range R32. For example, the imaging condition setting function 110a connects together, by using line segments, corresponding vertices of the imaging range R31 and the imaging range R32 that are rectangular and further sets the imaging range R33 that is also rectangular in such a manner that the middle points of the line segments serve as vertices thereof. The imaging range R33 is an example of the third imaging range.

After that, the imaging controlling function 110b is configured to cause the X-rays to be emitted from the X-ray generator 103 to each of the plurality of imaging ranges, while sequentially moving the X-ray detector 105. More specifically, at first, the imaging controlling function 110b adjusts the position of the X-ray generator 103 in terms of the Z direction and the X direction so that the X-rays are emitted onto the imaging range R31. Further, the imaging controlling function 110b adjusts the position of the X-ray detector 105 in terms of the Z direction and the X direction so as to be able to detect X-rays that have passed through the imaging range R31. After that, the imaging controlling function 110b performs an imaging process on the imaging range R31 by causing the X-rays to be emitted from the X-ray generator 103. In the same manner, the imaging controlling function 110b performs imaging processes on the imaging range R32 and the imaging range R33.

On the basis of the detection signal output from the X-ray detector 105, the image generating function 110c is configured to generate X-ray images respectively corresponding to the plurality of imaging ranges. Further, the image generating function 110c is configured to generate a long stitched image by combining together the X-ray images respectively corresponding to the plurality of imaging ranges.

Because the position coordinates of each of the imaging ranges are known, the image generating function 110c is able to combine together the X-ray images respectively corresponding to the plurality of imaging ranges on the basis of the position coordinates. However, because body movements of the patient are also expected during the imaging processes, the image generating function 110c may be configured to perform a position alignment by using an image recognition technique. For example, the image generating function 110c is capable of extracting a bone, a soft tissue, or the like as an anatomical feature point from the X-ray images and combining the X-ray images together in such a manner that the positions of the extracted feature point match each other.

As illustrated in FIG. 5, the imaging range R31, the imaging range R32, and the imaging range R33 are appropriate imaging ranges that sufficiently contain the spine having kyphosis. Further, although setting the imaging ranges requires the user's input operations, the input operations are easy. In other words, at the time of setting the imaging range R31 and the imaging range R32, there is no need to consider the overall shape of the spine, and it is possible to set the imaging ranges by considering only the point of the upper end or the lower end of the spine. As explained herein, by using the X-ray diagnosis apparatus 1 according to the embodiment, it is possible to set the plurality of imaging ranges for the long image stitching, easily and appropriately.

In a second embodiment, a modification example will be explained regarding the method for setting the region (the third imaging range) that connects together the imaging range R31 and the imaging range R32. More specifically, the imaging condition setting function 110a according to the second embodiment is configured to set a plurality of candidates for a third imaging range and to further set one of the plurality of candidates selected by the user as the third imaging range.

Figure 6A:
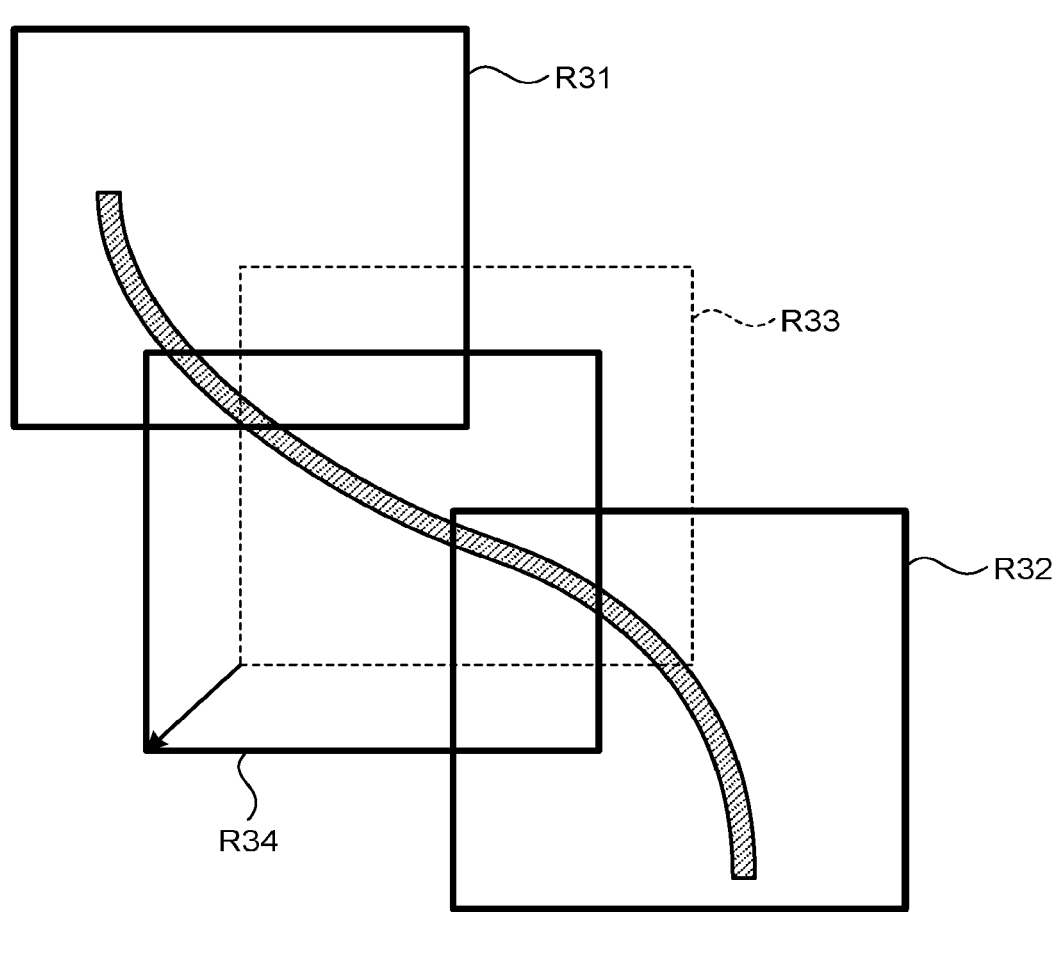
FIG. 6A illustrates an example of a candidate for a third imaging range according to a second embodiment.
Figure 6A:
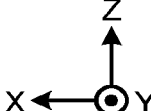
Figure 6B:
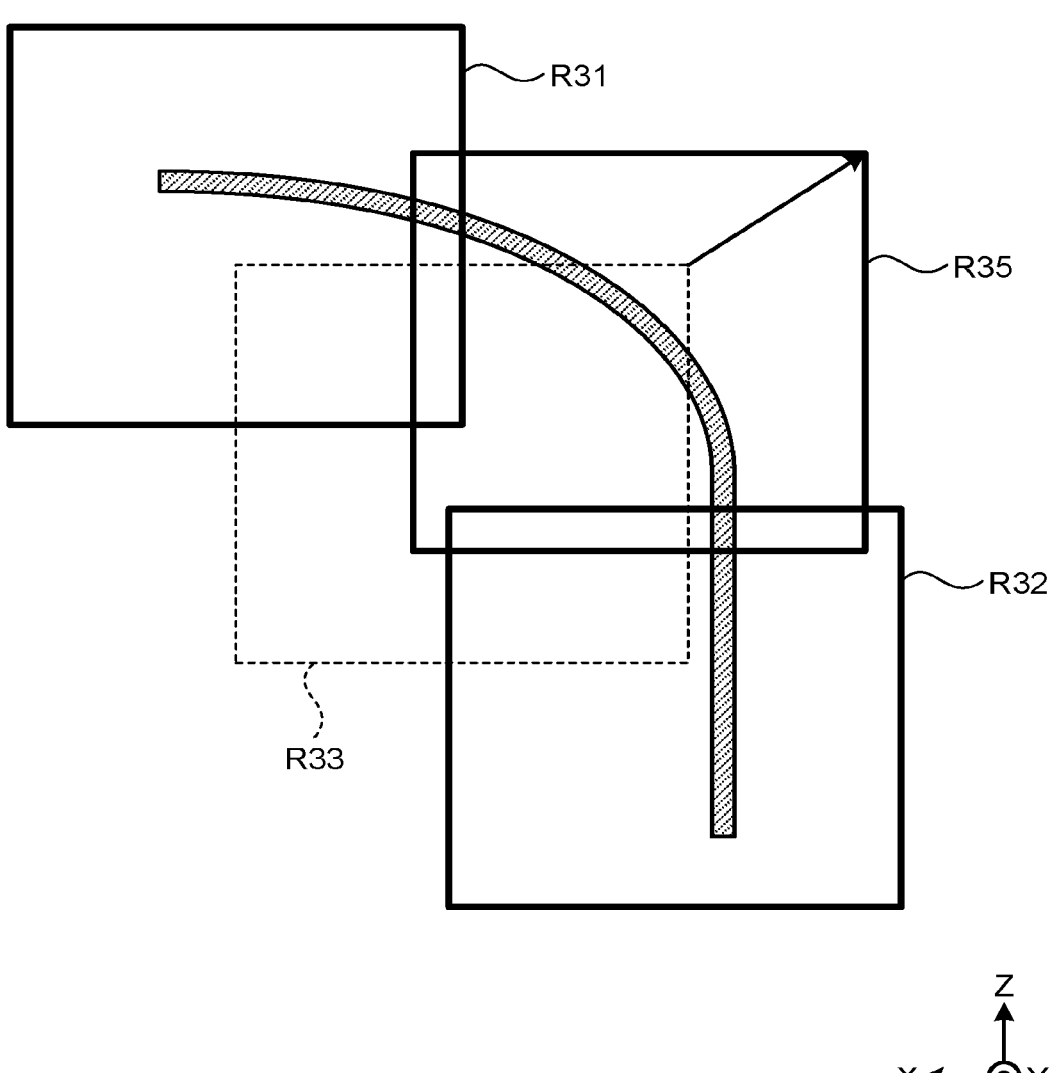
FIG. 6B illustrates another example of a candidate for the third imaging range according to the second embodiment.

As examples of the candidates for the third imaging range, FIG. 6A illustrates an imaging range R34, whereas FIG. 6B illustrates an imaging range R35. The imaging range R34 is a region obtained by moving the imaging range R33 in the +X direction and a −Y direction. Further, the imaging range R35 is a region obtained by moving the imaging range R33 in a −X direction and the +Y direction.

The candidates for the third imaging range are set so as to each at least partially overlap with the imaging range R31 and with the imaging range R32. For example, the imaging condition setting function 110a is configured to connect together, by using line segments, corresponding vertices of the imaging range R31 and the imaging range R32 that are rectangular and to further set the imaging range R33 that is also rectangular in such a manner that the middle points of the line segments serve as vertices thereof. Further, by moving the imaging range R33 in prescribed directions by prescribed distances, the imaging condition setting function 110a is configured to set the imaging range R34 and the imaging range R35.

For example, as the candidates for the third imaging range, the output function 110d is configured to cause the display 108 to display the imaging range R33, the imaging range R34, and the imaging range R35. For example, the output function 110d is configured to cause the display 108 to display the imaging range R33, the imaging range R34, and the imaging range R35 so as to be superimposed on an optical image taken of the patient. In an example, the output function 110d is configured to cause a superimposition image to be displayed in which the imaging range R33, the imaging range R34, and the imaging range R35 are superimposed on the optical image. In another example, the output function 110d may be configured to display a superimposition image in which the imaging range R33 is superimposed on the optical image, another superimposition image in which the imaging range R34 is superimposed on the optical image, and yet another superimposition image in which the imaging range R35 is superimposed on the optical image. The user selects an appropriate imaging range from among these candidates via the input interface 107, so that the imaging condition setting function 110a sets the selected imaging range as the third imaging range. For example, by looking at the patient and estimating the shape of the spine, the user is able to select the imaging range R34 when the spine is expected to have a shape like the curve in FIG. 6A and to select the imaging range R35 when the spine is expected to have a shape like the curve in FIG. 6B. It is also acceptable to enable the user to further adjust the position of the selected imaging range, after selecting one of the imaging ranges.

In yet another example, the imaging condition setting function 110a may be configured to employ a projector, for example, to project the imaging range R33, the imaging range R34, and the imaging range R35 that were set as the candidates for the third imaging range, onto the patient. For example, the imaging condition setting function 110a may project each of the imaging ranges R33, R34, and R35 onto the patient, by switching from one to another, as appropriate, in accordance with input operations performed by the user. After that, the user selects one of the imaging ranges R33, R34, and R35 being projected, so that the imaging condition setting function 110a sets the selected imaging range as the third imaging range.

Further, it is also acceptable to vary the quantity of contained imaging ranges among the candidates for the third imaging range. For example, as illustrated in FIG. 6B, the area by which the imaging range R35 overlaps with the imaging range R31 and with the imaging range R32 is smaller than that of the imaging range R33 or the imaging range R34. The smaller the overlapping area is, the more difficult it may be to perform the position alignment on the basis of an anatomical feature point. Thus, the precision of the process of obtaining a combined long stitched image may be degraded.

For this reason, the imaging condition setting function 110a may be configured to determine a plurality of imaging ranges that overlap with the imaging range R31 and with the imaging range R32 by sufficient areas, as candidates for the third imaging range. For example, the imaging condition setting function 110a may set the following two ranges as the candidates for the third imaging range: an imaging range that overlaps with the imaging range R31 by a sufficient area; and another imaging range that overlaps with the aforementioned imaging range and with the imaging range R33 by sufficient areas.

According to the second embodiment, it is possible to select the third imaging range more appropriately from among the plurality of candidates. In that situation, the operation performed by the user is to select one of the candidates while referring to a general position of a central part of the spine and is relatively easy without the need to consider the overall shape of the spine. As explained herein, by using the X-ray diagnosis apparatus 1 according to the second embodiment, it is possible to set the plurality of imaging ranges for the long image stitching, easily and more appropriately.

In the first and the second embodiments described above, the example was explained in which the plurality of imaging ranges touching each other are set, by using the imaging range R31 and the imaging range R32 as the reference information. In a third embodiment, an example will be explained in which a plurality of imaging ranges touching each other are set by using an optical image taken of the patient as reference information.

Figure 7A:
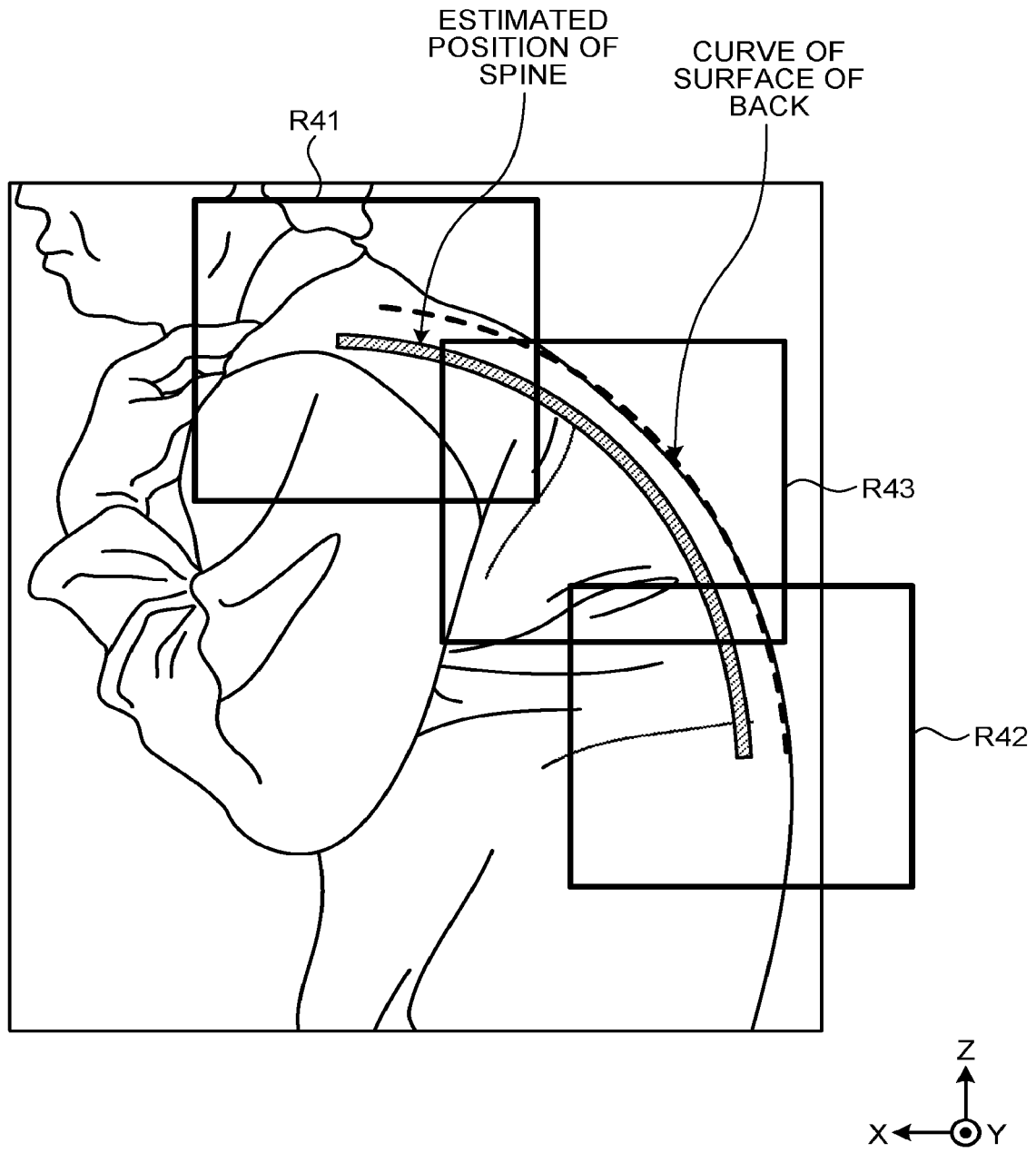
FIG. 7A is a drawing for explaining a method for setting a plurality of imaging ranges according to a third embodiment.

FIG. 7A illustrates an example of an optical image taken of the patient. For example, the X-ray generator 103 is provided with a camera, so that the camera takes the optical image of the patient positioned between the X-ray generator 103 and the X-ray detector 105. In the optical image, the curve of the surface of the patient's back is rendered.

Figure 7B:
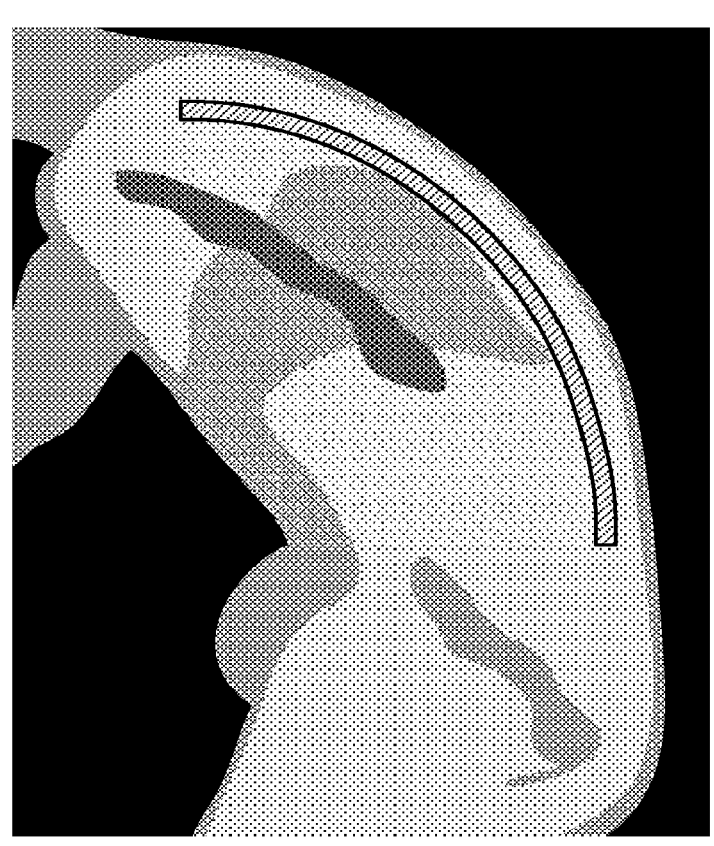
FIG. 7B is another drawing for explaining the method for setting the plurality of imaging ranges according to the third embodiment.
Figure 7B:
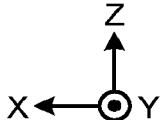

In this situation, the curve of the surface of the back and the spine extend substantially parallel to each other, as illustrated in FIGS. 7A and 7B. Accordingly, the imaging condition setting function 110a is able to estimate the position of the spine, on the basis of the curve of the surface of the back. For example, the imaging condition setting function 110a is configured to estimate the position of the spine, by approximating the curve of the surface of the back to an arc and further reducing the size of the arc while maintaining the center thereof.

Further, the imaging condition setting function 110a is configured to set a plurality of imaging ranges touching each other for long image stitching, on the basis of the estimated position of the spine. For example, the imaging condition setting function 110a is configured to set an imaging range R41 in FIG. 7A so that the upper end of the estimated spine in terms of the Z direction is contained substantially at the center thereof and to set an imaging range R42 so that the lower end of the estimated spine in terms of the Z direction is contained substantially at the center thereof. After that, the imaging condition setting function 110a is configured to set an imaging range R43 so as to connect together the imaging range R41 and the imaging range R42.

For example, the imaging condition setting function 110a is configured to set the imaging range R43 so that the estimated position of the spine shape is contained substantially at the center thereof. For example, the imaging condition setting function 110a is configured to set the imaging range R43 so as to overlap with the imaging range R41 and with the imaging range R42 by sufficient areas, to enable a position alignment based on an anatomical feature point. In an example, the imaging condition setting function 110a may be configured to receive a correction made by the user on the set imaging ranges.

According to the third embodiment described above, it is possible to automate the imaging range setting process. In addition, even when the spine has a large curve, it is possible to set the plurality of imaging ranges without having the spine sticking out. As explained herein, by using the X-ray diagnosis apparatus 1 according to the third embodiment, it is possible to set the plurality of imaging ranges for the long image stitching, easily and appropriately.

In the first to the third embodiments described above, the example was explained in which all the imaging ranges are set before the imaging process is started. In a fourth embodiment, an example will be explained in which only one or more of the imaging ranges are set before the imaging process is started, and the rest of the imaging ranges is set after the one or more imaging ranges are imaged.

Figure 8:
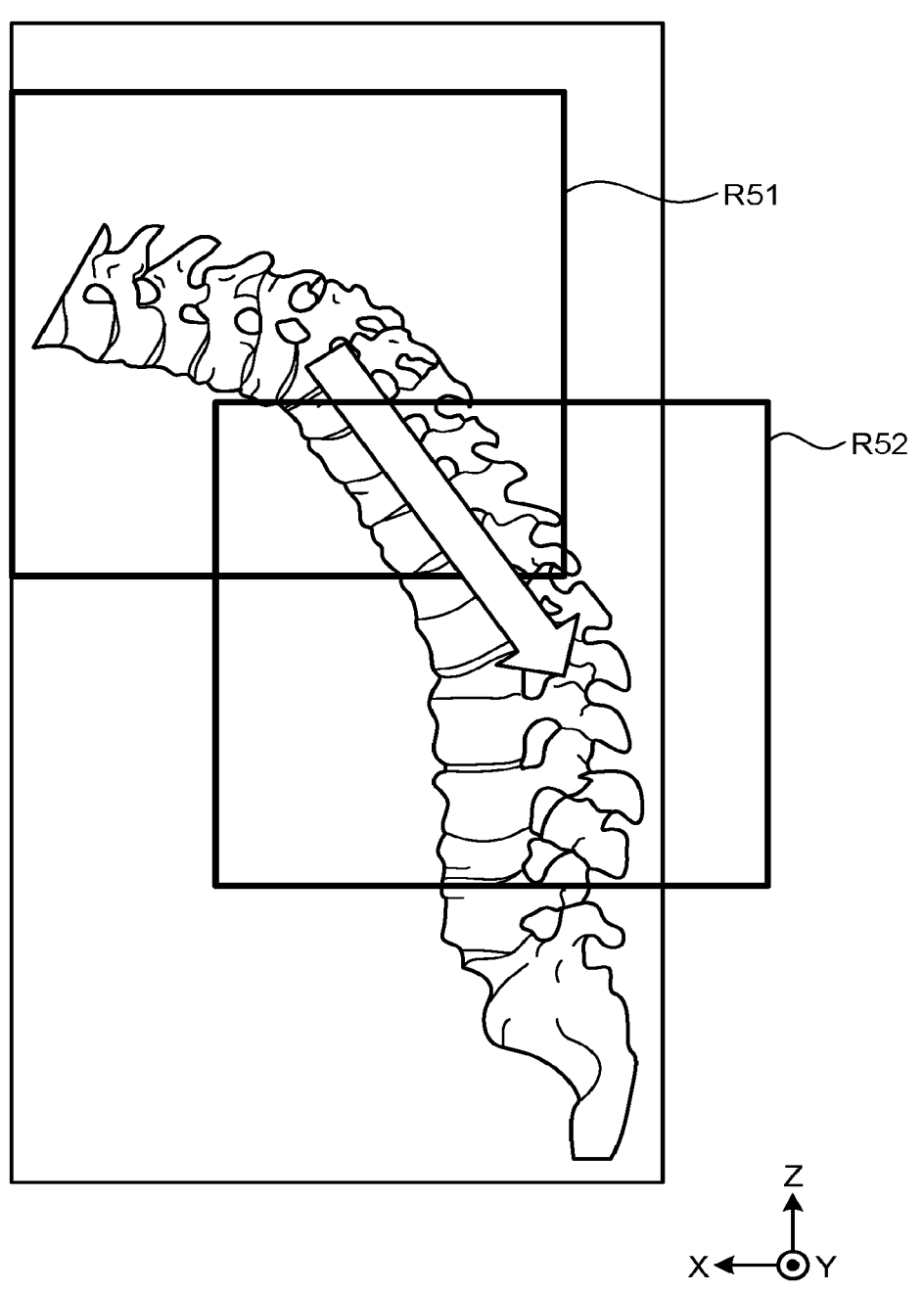
FIG. 8 is a drawing for explaining a method for setting a plurality of imaging ranges according to a fourth embodiment.

To begin with, the imaging condition setting function 110a is configured to set an imaging range R51 in FIG. 8. More specifically, the imaging condition setting function 110a is configured to set the imaging range R51 so that an end part of the spine of the patient in terms of the Z direction is contained therein. For example, the user (e.g., a medical doctor) moves the position of the X-ray generator 103 via the input interface 107, while referring to the visible light indicating the imaging range and realized with the laser emission from the light source provided for the X-ray generator 103, and further performs an input operation to confirm a position determined to be appropriate. On the basis of the input operation of the user, the imaging condition setting function 110a is able to set the imaging range R51.

Subsequently, the imaging controlling function 110b is configured to image the imaging range R51. In other words, the imaging controlling function 110b is configured to cause X-rays to be emitted from the X-ray generator 103 onto the imaging range R51 and to cause the X-ray detector 105 to detect X-rays that have passed through the imaging range R51. Further, the image generating function 110c is configured to generate an X-ray image of the imaging range R51 on the basis of a detection signal output from the X-ray detector 105. The X-ray image of the imaging range R51 is an example of the end part X-ray image.

After that, the imaging condition setting function 110a is configured to extract the shape of the spine appearing in the X-ray image of the imaging range R51 and to estimate the shape of the spine outside the imaging range R51 on the basis of the extracted shape. For example, the imaging condition setting function 110a is configured to approximate the shape of the spine appearing in the X-ray image of the imaging range R51 to an arc and to further expand the shape in a –Z direction in FIG. 8. Alternatively, for example, the imaging condition setting function 110a may estimate the shape of the spine outside the imaging range R51, by selecting a spine shape that matches the spine shape appearing in the X-ray image of the imaging range R51 from among long stitched images of the entire spines of other patients taken in the past.

Further, according to the estimated shape, the imaging condition setting function 110a is configured to set an imaging range R52 that partially overlaps with the imaging range R51. For example, the imaging range R52 is set so that the estimated position of the spine is at the center thereof, while the imaging range R52 overlaps with the imaging range R51 by a sufficient area, to sufficiently enable a position alignment based on an anatomical feature point.

After the imaging range R52 is set, the imaging process and the imaging range setting process may be repeated until the entire spine is imaged, for example. In other words, after the imaging range R52 is set, the imaging controlling function 110b images the imaging range R52, so that the image generating function 110c generates an X-ray image of the imaging range R52. On the basis of the shape of the spine appearing in the X-ray image of the imaging range R52, the imaging condition setting function 110a further sets an imaging range that partially overlaps with the imaging range R52.

According to the fourth embodiment described above, although the user operation is required at the time of setting the imaging range R51, it is possible to have the rest of the imaging ranges set automatically. Further, at the time of setting the imaging range R51, the user does not need to consider the overall shape of the spine, and needs to consider only the point of the one end of the spine. Thus, setting the imaging range R51 is easy. In addition, even when the spine has a large curve, it is possible to set the plurality of imaging ranges without having the spine sticking out. As explained herein, by using the X-ray diagnosis apparatus 1 according to the embodiment, it is possible to set the plurality of imaging ranges for the long image stitching, easily and appropriately.

Besides the embodiments described above, it is possible to carry out the present disclosure by applying various modifications thereto.

For instance, although the example was explained in the above embodiments in which the X-ray generator 103 is configured to be movable in the Z direction and the X direction, the position of the X-ray generator 103 may be fixed.

When the position of the X-ray generator 103 is fixed, the imaging controlling function 110b may be configured to vary the angle of the X-ray generator 103 so that the X-rays are emitted onto the set imaging ranges. More specifically, the imaging controlling function 110b may be configured to cause the X-rays to be emitted onto the set imaging ranges, by varying the position of the emission opening with respect to the position of an X-ray focal point of the X-ray tube, so as to vary the emission angle.

In another example, the imaging controlling function 110*b* may be configured to control the X-ray limiter of the X-ray generator 103, so that the X-rays are emitted onto the set imaging ranges. For example, the imaging controlling function 110*b* may be configured to cause the X-rays to be emitted onto the set imaging ranges, by sliding and moving the limiting blades so as to move the position of the emission opening formed by the limiting blades.

Further, in the embodiments described above, the example was explained in which the patient was imaged from a side so as to acquire the X-ray image taken on the sagittal plane; however, possible embodiments are not limited to this example. For instance, the present disclosure is similarly applicable to the situation where a patient is imaged from the front so as to acquire an X-ray image taken on a coronal plane. In that situation, for example, it is possible to acquire a long stitched image to be used for diagnosing scoliosis of the spine, for example.

Further, in the embodiments described above, the example was explained in which the spine is the examined site; however, possible embodiments are not limited to this example. For instance, the present disclosure is similarly applicable to a medical examination performed on a leg of a patient.

Further, in the embodiments described above, the example was explained in which the X-ray generator 103 and the X-ray detector 105 are arranged as illustrated in FIG. 1, so as to image the patient in a standing or sitting position; however, possible embodiments are not limited to this example. For instance, the present disclosure is similarly applicable to a medical examination performed on a patient in a decubitus position lying on a table. In that situation, for example, the longitudinal direction of the table (i.e., the body axis direction of the patient) serves as the first direction. In other words, the X-ray detector 105 has a detection surface extending parallel to the longitudinal direction of the table and is configured to be movable in the longitudinal direction and in the direction orthogonal to the longitudinal direction and parallel to the detection surface.

The term "processor" used in the above explanation denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). When the processor is a CPU, for example, the processor is configured to realize the functions by reading and executing the programs saved in storage circuitry. In contrast, when the processor is an ASIC, for example, instead of having the programs saved in the storage circuitry, the functions are directly incorporated in the circuitry of the processor as logic circuitry. Further, the processors according to the embodiments do not each necessarily have to be structured as a single piece of circuitry. It is also acceptable to structure a single processor by combining together a plurality of pieces of independent circuitry, so as to realize the functions thereof. Furthermore, it is also acceptable to integrate two or more of the constituent elements illustrated in any of the drawings into a single processor so as to realize the functions thereof.

Further, the example was explained above in which the single memory is configured to store therein the programs corresponding to the processing functions of the processing circuitry; however, possible embodiments are not limited to this example. For instance, it is also acceptable to provide a plurality of memory elements in a distributed manner, while the processing circuitry is configured to read a corresponding program from each of the individual memory elements. Further, instead of having the programs saved in the one or more memory elements, it is also acceptable to directly incorporate the programs in the circuitry of one or more processors. In that situation, the one or more processors are configured to realize the functions by reading and executing the programs incorporated in the circuitry thereof.

The constituent elements of the apparatuses in the above embodiments are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Further, it is possible to realize the methods explained in the above embodiments, by causing a computer such as a personal computer or a workstation to execute a program prepared in advance. It is also possible to distribute the program via a network such as the Internet. Further, it is also possible to execute the program, by having the program recorded on a computer-readable non-transitory recording medium such as a hard disk, a flexible disk (FD), a Compact Disk Read-Only Memory (CD-ROM), a Magneto Optical (MO) disk, a Digital Versatile Disk (DVD), or the like, so as to have the program read by a computer from the recording medium.

According to at least one aspect of the embodiments described above, it is possible to set the plurality of imaging ranges for the long image stitching, easily and appropriately.

By using the X-ray diagnosis apparatus according to at least one aspect of the embodiments, it is possible to set the plurality of imaging ranges for the long image stitching, easily and appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:
an X-ray generator configured to emit X-rays;
an X-ray detector having a detection surface parallel to a first direction and being movable in the first direction and in a second direction orthogonal to the first direction and parallel to the detection surface; and
processing circuitry configured to
set a plurality of imaging ranges touching each other based on reference information,
cause the X-rays to be emitted from the X-ray generator to each of the plurality of imaging ranges while sequentially moving the X-ray detector, and generate X-ray images respectively corresponding to the plurality of imaging ranges, based on a detection signal resulting from the X-ray detector detecting the X-rays, wherein as the reference information, the processing circuitry is further configured to set a first imaging range so that an upper end, in terms of the first direction, of an examined site of an examined subject, is contained substantially at a center thereof in terms of the second direction, and set a second imaging range so that a lower end, in terms of the first direction, of the examined site is contained substantially at a center thereof in terms of the second direction, and the processing circuitry is further configured to set the plurality of imaging ranges by setting at least one third imaging range that connects together the first imaging range and the second imaging range.

2. The X-ray diagnosis apparatus according to claim 1, wherein the processing circuitry is further configured to set a plurality of candidates for the third imaging range and to set one of the plurality of candidates selected by a user as the third imaging range.

3. The X-ray diagnosis apparatus according to claim 2, wherein the processing circuitry is further configured to set a quantity of imaging ranges for each of the candidates.

4. The X-ray diagnosis apparatus according to claim 2, wherein the processing circuitry is further configured to further cause a display to display the plurality of candidates, and as the third imaging range, the processing circuitry is further configured to set the candidate selected by the user referencing the display, from among the plurality of candidates displayed by the display.

5. The X-ray diagnosis apparatus according to claim 4, wherein the processing circuitry is further configured to cause the plurality of candidates to be displayed so as to be superimposed on an optical image taken of the examined subject.

6. The X-ray diagnosis apparatus according to claim 2, wherein the processing circuitry is further configured to project the plurality of candidates onto the examined subject and to set, as the third imaging range, the one of the candidates selected by the user referencing the projection.

7. An X-ray diagnosis apparatus, comprising:

an X-ray generator configured to emit X-rays;

an X-ray detector having a detection surface parallel to a first direction and being movable in the first direction and in a second direction orthogonal to the first direction and parallel to the detection surface; and processing circuitry configured to set a plurality of imaging ranges touching each other based on reference information, cause the X-rays to be emitted from the X-ray generator to each of the plurality of imaging ranges while sequentially moving the X-ray detector, and generate X-ray images respectively corresponding to the plurality of imaging ranges, based on a detection signal resulting from the X-ray detector detecting the X-rays, wherein the reference information is an optical image taken of an examined subject that renders a curve of a surface of a back of the examined subject, and the processing circuitry is further configured to set the plurality of imaging ranges, by approximating the curve of the surface of the back to an arc, reducing a size of the arc while maintaining a center, and estimating a position of a spine as an examined site.

8. An X-ray diagnosis apparatus, comprising:

an X-ray generator configured to emit X-rays;

an X-ray detector having a detection surface parallel to a first direction and being movable in the first direction and in a second direction orthogonal to the first direction and parallel to the detection surface; and processing circuitry configured to set a plurality of imaging ranges touching each other based on reference information, cause the X-rays to be emitted from the X-ray generator to each of the plurality of imaging ranges while sequentially moving the X-ray detector, and generate X-ray images respectively corresponding to the plurality of imaging ranges, based on a detection signal resulting from the X-ray detector detecting the X-rays, wherein the reference information is an end part X-ray image acquired of a first imaging range provided so as to contain an end, in terms of the first direction, of a spine of an examined subject, and the processing circuitry is further configured to set the plurality of imaging ranges by setting at least one imaging range connected to the first imaging range, (a) by approximating a shape of the spine appearing in the end part X-ray image to an arc, expanding the shape in the first direction and estimating a position of a part of the spine of the examined subject that is not contained in the end part X-ray image, or (b) by selecting a spine shape that matches the shape of the spine appearing in the end part X-ray image from among images of entire spines of other patients taken in the past and estimating a position of a part of the spine of the examined subject that is not contained in the end part X-ray image.

* * * * *